United States Patent [19]
Gram et al.

[11] Patent Number: 5,461,236
[45] Date of Patent: Oct. 24, 1995

[54] OIL SPILL DETECTION SYSTEM

[75] Inventors: Herbert R. Gram, 287 Boston Post Rd., Madison, Conn. 06443; Mathew P. Jadamec, Mystic; Jonathan W. Johnson, Madison, both of Conn.

[73] Assignees: Herbert R. Gram; Joan F. Gram, both of Madison, Conn.

[21] Appl. No.: 896,403

[22] Filed: Jun. 9, 1992

[51] Int. Cl.$^6$ .......................... G01N 21/64; G01N 21/85
[52] U.S. Cl. ................... 250/461.1; 250/301; 250/458.1
[58] Field of Search .................... 250/301, 458.1, 250/459.1, 461.1, 573, 461.2; 356/442; 340/984, 850; 73/170.04, 170.09; 441/11, 16, 20

[56] References Cited

U.S. PATENT DOCUMENTS

| | | | |
|---|---|---|---|
| 3,043,908 | 7/1962 | Madsen | 250/253 |
| 3,839,639 | 10/1974 | Hughes | 250/461.1 |
| 3,899,213 | 8/1975 | Fantasia et al. | 250/461.1 |
| 4,006,360 | 2/1977 | Mueller | 250/461.2 |
| 4,116,045 | 9/1978 | Potter | 340/605 |
| 4,290,043 | 9/1981 | Kaplan | 250/342 |
| 4,573,796 | 3/1986 | Martin et al. | 250/461.2 |
| 4,814,614 | 3/1989 | Tsui | 250/301 |
| 5,007,285 | 4/1991 | Dahlen et al. | 441/3 |
| 5,097,135 | 3/1992 | Makino et al. | 250/461.1 |
| 5,102,625 | 4/1992 | Milo | 250/461.1 |
| 5,208,465 | 5/1993 | Jacobson | 250/573 |
| 5,281,826 | 1/1994 | Ivancic et al. | 250/458.1 |

OTHER PUBLICATIONS

Gram, Herbert R., "The Remote Detection and Identification of Surface Oil Spills", Second Conference on Environmental Quality Sensors by the Environmental Protection Agency held Oct. 10–11, 1973 in Las Vegas, Nevada.

Jadamec, J. Richard, "Single Wavelength Fluorescence Excitation For On–Site Oil Spill Identification", Second Conference On Envrionmetnal Quality Sensors held Oct. 10–11, 1973 in Las Vegas, Nevada.

Gram, Herbert R., "The Remote Detection and Identification of Surface Oil Spills", 25th Pittsburgh Conference on Analytical Chemistry and Applied Spectroscopy held Mar. 4–8, 1974 in Cleveland, Ohio.

Gram, Herbert R., "An Extended Capability Buoy for the Detection of Oil Spills" 27th Pittsburgh Conference on Analytical Chemistry an Applied Spectroscopy held Mar. 3–7, 1975 in Cleveland, Ohio.

Coakley, William A., "Comparative Identification of Oil Spills by Fluorescence Fingerprinting".

*Primary Examiner*—Constantine Hannaher
*Attorney, Agent, or Firm*—St. Onge Steward Johnston & Reens

[57] ABSTRACT

A sensor for the reliable detection of oil spills using fluorescence techniques. An ultraviolet (UV) light source is located around an optical column with which selected wavelengths of fluorescing hydrocarbons or other substances can be detected. The source of UV light is held at a constant level and special techniques are employed to remove background optical noise from the various detected wavelength signals. Short and long term running averages are generated to detect oil spills. A special buoy is employed to allow the sensor to be oriented at a cavity in the buoy to reliable detect oil spills on waterways. The buoy has windows to enable surface water to freely pass through into the cavity while preventing turbulence from open water waves and wind. The buoy has a low center of gravity well below the water line with a large submerged segment to reduce heaving motions and provide a stable platform for the detection of fluorescing substances.

12 Claims, 13 Drawing Sheets

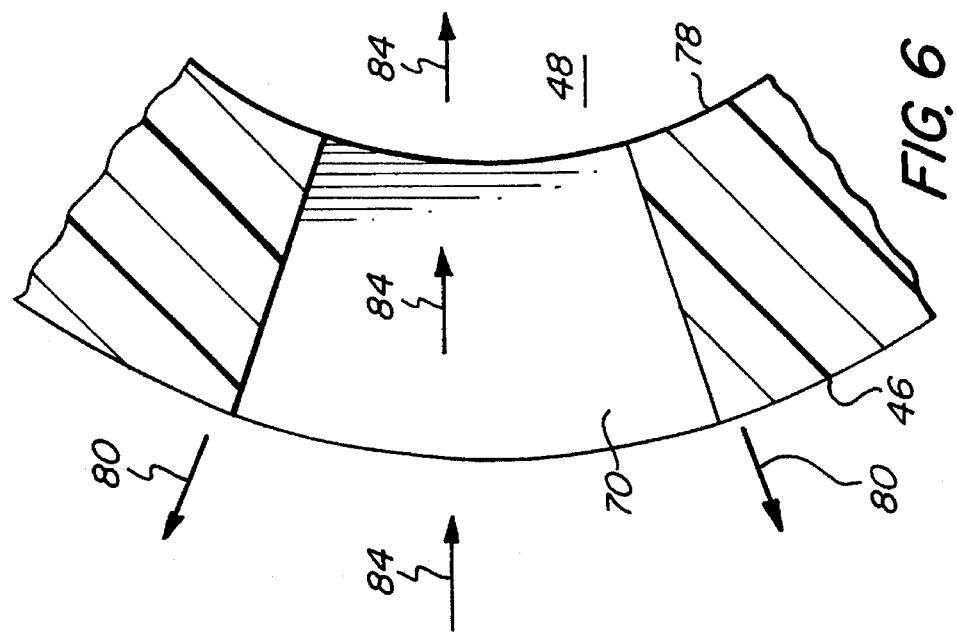
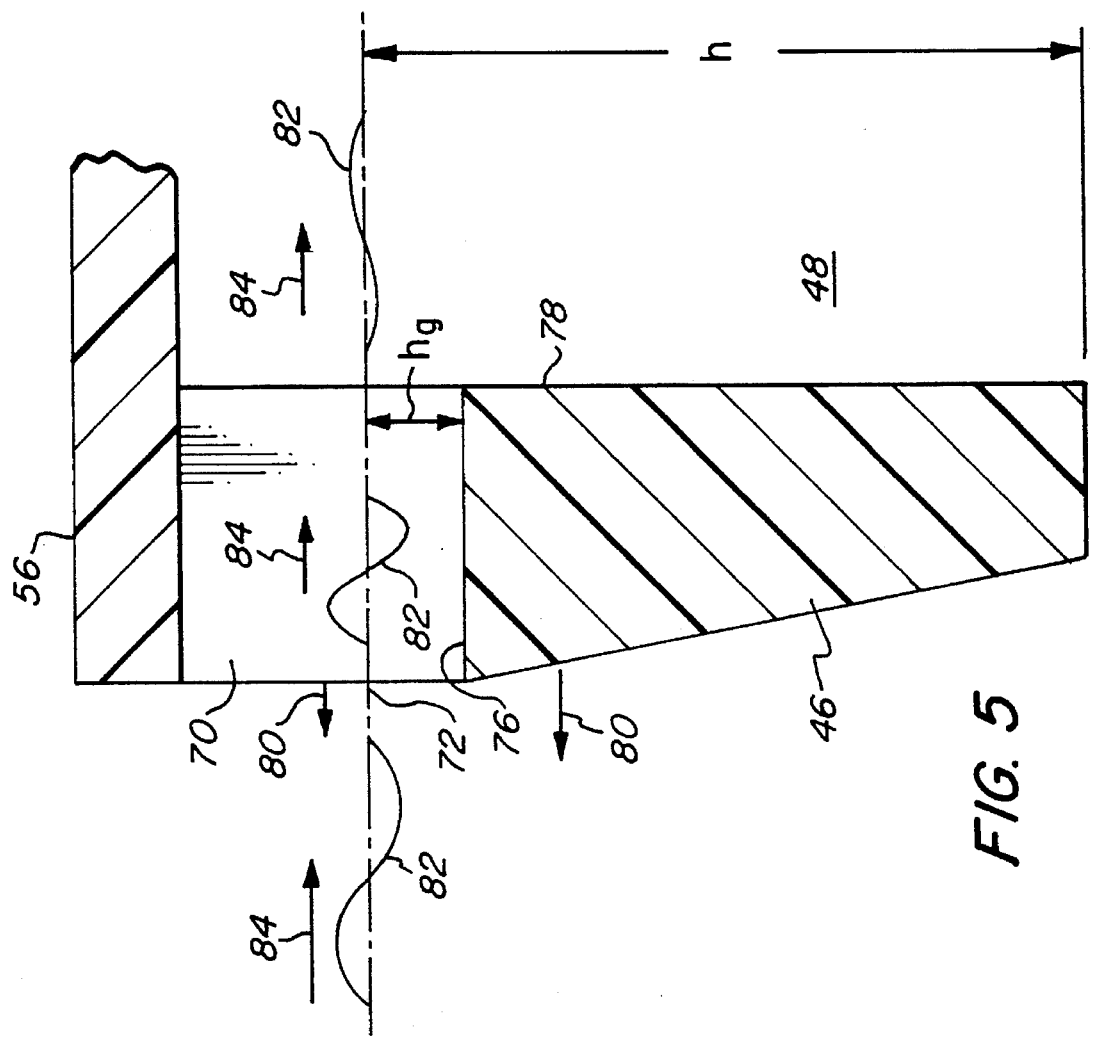

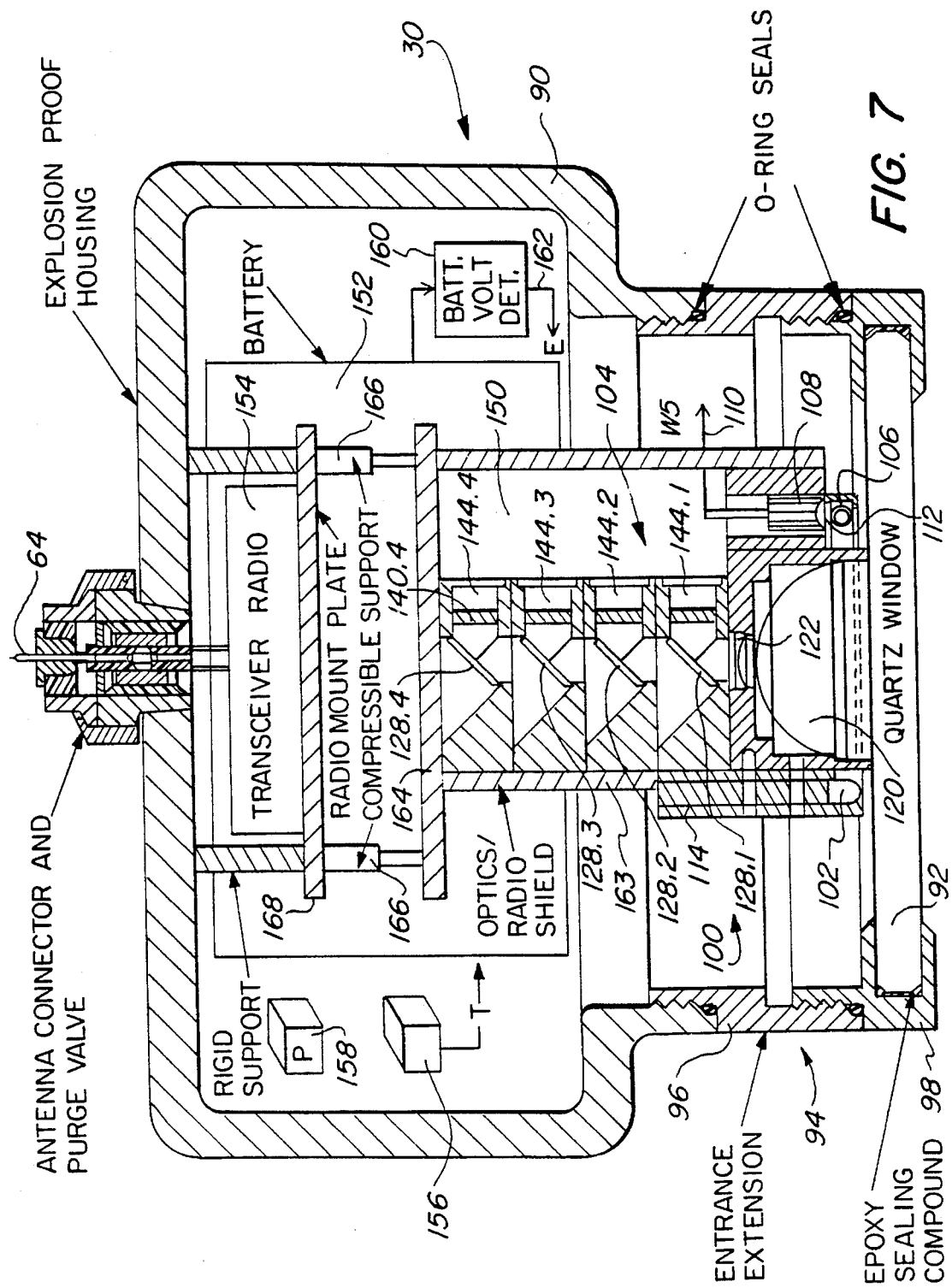

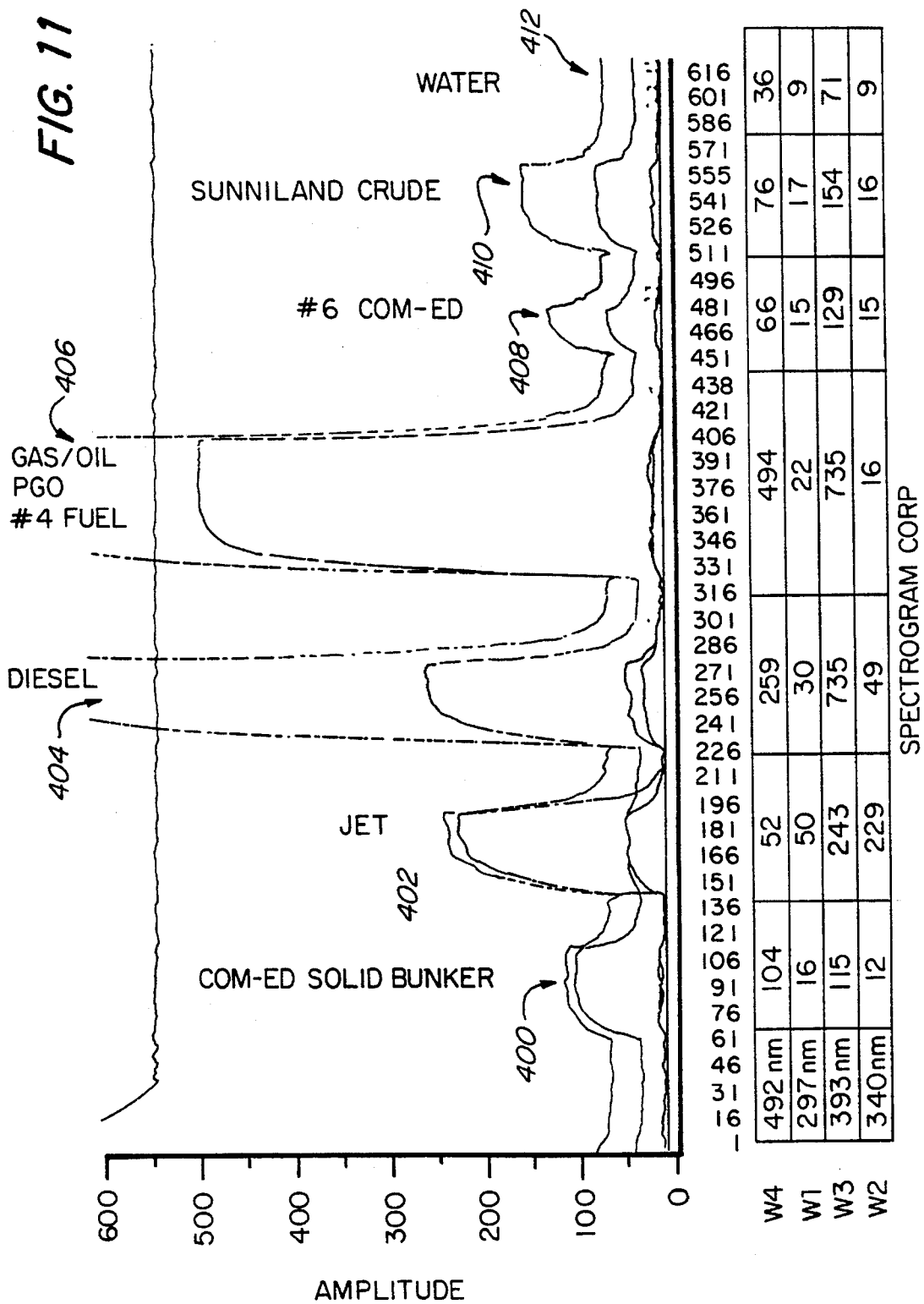

OIL SPILL DETECTION SYSTEM

FIELD OF THE INVENTION

This invention generally relates to a technique for the detection of chemicals such as oil, and more specifically, to a method and apparatus for the detection of chemical spills on waterways.

BACKGROUND OF THE INVENTION

Fluorometers are known instruments with which the fluorescence and phosphorescence characteristics of chemicals in response to the exposure of ultraviolet (UV) light can be measured. Such instruments are commonly referred to as fluorescence spectrophotometers. Articles have been published on various fluorescence analysis of oils in response to UV radiation. See, for example, a 1973 publication entitled, "Single Wavelength Fluorescence Excitation For On-Site Oil Spill Identification", authored by J. Richard Jadamec and presented as part of the Proceedings of the Second Conference On Environmental Quality Sensors held Oct. 10–11, 1973, in Las Vegas, Nev., and sponsored by the U.S. Environmental Protection Agency, Offices of Research and Development and Monitoring Systems. Of interest is an article published by William A. Coakley entitled, "Comparative Identification Of Oil Spills by Fluorescence Fingerprinting".

During the early seventies, a fluorescent oil detector system was developed to detect spills of a specific type of oil, a No. 6 fuel. An article on the buoy system was published and presented by one of the inventors of this application at the 15th and 27th Pittsburgh Conferences On Analytical Chemistry And Applied Spectroscopy held in Cleveland, Ohio, respectively on Mar. 4–8, 1974 and Mar. 3–7, 1975. The buoy involved a central sensor support structure which placed a UV light source and a fluorescence detector a short distance above the water line. A number of buoy floating arms extended out from the central structure. The system was capable of detecting the No. 6 fuel during day and night time.

Although fluorescence techniques for the detection of oil spills have been developed, a need exists to enable a reliable and rapid detection and analysis of oil so as to alert an operator of the occurrence of a spill with a minimum of false alarms. This would enable an operator to monitor a plurality of sensors distributed at a variety of key locations around oil shipping tankers, at discharge docks, or at farms where many storage tanks are located.

SUMMARY OF THE INVENTION

With a fluorescence spectroscopy sensor in accordance with the invention, chemicals, such as oils, can be rapidly and reliably detected and characterized as being of a particular type. This is achieved by employing a UV lamp light source which excites a surface to be examined with light which is predominantly rich in energy at a particular wavelength. Optical filters are then used to select predetermined wavelengths from any fluorescence emanating from the illuminated surface and the filtered light is detected to produce electrical signals whose amplitudes are representative of the magnitude of the detected fluorescence. A detector is employed to produce a signal representative of the temperature of the gas inside the UV lamp. This signal is then compared with a reference level to produce an error signal indicative of whether the gas inside the lamp is at the proper temperature. The error signal is then used to vary the power to the UV lamp in such a direction as to reduce the error to a minimum.

With an accurate control over the intensity level of the excitation wavelength, the magnitude levels derived from the various detectors can be reliably used in the determination of the presence of a fluorescing oil and enable the determination of the type that is detected.

A sensor in accordance with the invention can be reliably employed in a broad range of ambient conditions, such as during day or night and in the presence of night light sources which generate large amounts of UV light and with diverse back scattering conditions and in the presence of normal background fluorescence from water biota. This is achieved as more particularly described herein for one embodiment of the invention by deriving, for each of the selected fluorescing wavelengths, signals representative of the background level of ambient light noise. This background level is then removed from the detected fluorescing wavelength signals to provide a clear indication of the condition of the surface being monitored. If an oil spill were then to occur on the surface, a change in the fluorescence behavior of the surface would be detected and an alarm generated.

By use of the generation of signals representative of the background ambient noise level, a sensor in accordance with the invention can be advantageously employed in the transportation of different oils through a common pipeline to different outlets. Or, the sensor can be used to protect engines used at power plants and the like from being inadvertently fed with a disastrously wrong fuel. In both of these cases, a sensor of this invention is used to monitor a pipeline through which oil or fuel passes. The sensor can then detect when a different oil or fuel passes through the pipeline and provide an indication to the operator located at a pipeline outlet to change valve settings or an alarm to protect the engine from being fed with the wrong fuel. With a sensor of this invention, materials which have been doped with a fluorescing material can be traced by not only detecting the fluorescing substance but also by identifying it.

With a sensor in accordance with the invention, flexibility is provided in the selection of parameters and display of monitoring areas. Individual sensors can be remotely adjusted with different sets of criteria to suit different conditions. Sensors can be portable, self-contained devices.

A particularly advantageous feature of the invention resides is the use of a buoy that is adapted to provide a stable, relatively quiet observation zone through which surface water can pass without disturbance of the sensor's ability to detect oil spills on the water throughout a broad range of weather conditions. The buoy involves a floating structure which surrounds an inner cavity. The buoy wall surrounding the cavity has windows which extend below the water line to enable surface water to freely move into the cavity. A fluorescent spectroscopy sensor in accordance with the invention is mounted inside the cavity to monitor its water surface.

The windows and the buoy wall are formed so as to substantially attenuate and reflect incident waves from the surrounding open water and thus maintain a relatively calm interior water surface. The windows are further shaped so as to reduce light interference from the sun and surrounding night lights and enable the fluorescence spectrometry sensor to provide a reliable detection of oil or other chemical spills.

It is, therefore, an object of the invention to provide a fluorescent spectrometry sensor with which substances such as oils can be reliably detected. It is a further object of the invention to provide a buoy system with which spills on inlets and waterways of chemicals such as oil can be reliably detected with a low incidence of false alarms. It is still further an object of the invention to enable the detection and recognition of a diversity of different oils and use the information in an industrial process, such as the protection of equipment and the control of a pipeline. It is still further an object of the invention to provide a fluorescence sensor with which particular fluorescing materials can be used as dopants and then detected and identified.

These and other objects and advantages of the invention can be understood from the following detailed description of several embodiments of the invention as shown in the drawings.

DETAILED DESCRIPTION OF DRAWINGS

FIG. 5 is a partial vertical section view of the buoy of FIG. 2;

FIG. 6 is a partial horizontal view of the buoy window illustrated in FIG. 5;

FIG. 7 is a vertical sectional view of the sensor used in the buoy system of FIG. 2;

Figures 8, 9:
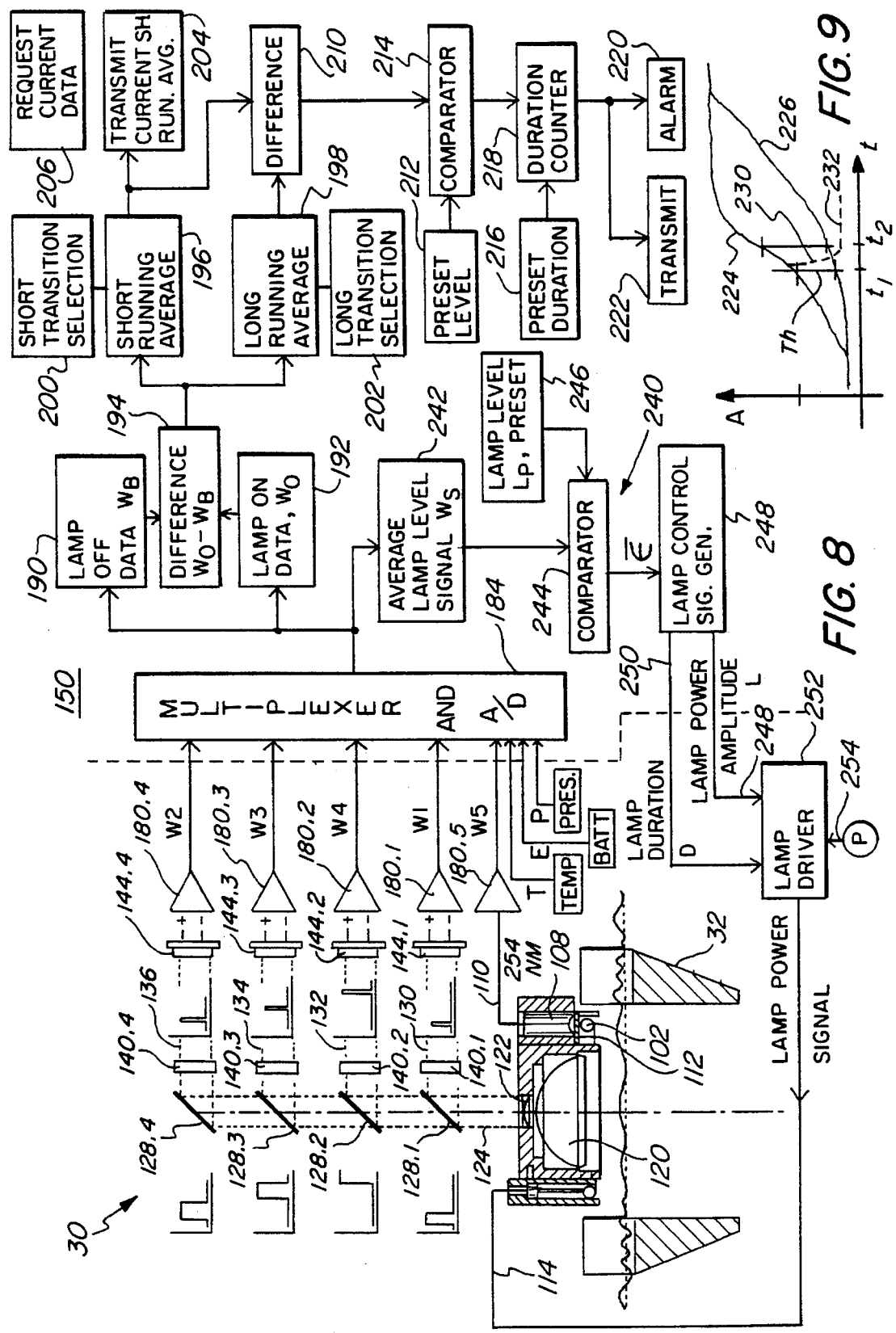
FIG. 8 is a schematic block diagram of a buoy system in accordance with the invention.
FIG. 9 is a plot of sensor responses obtained with the sensor of FIGS. 7 and 8.
Figure 10A:
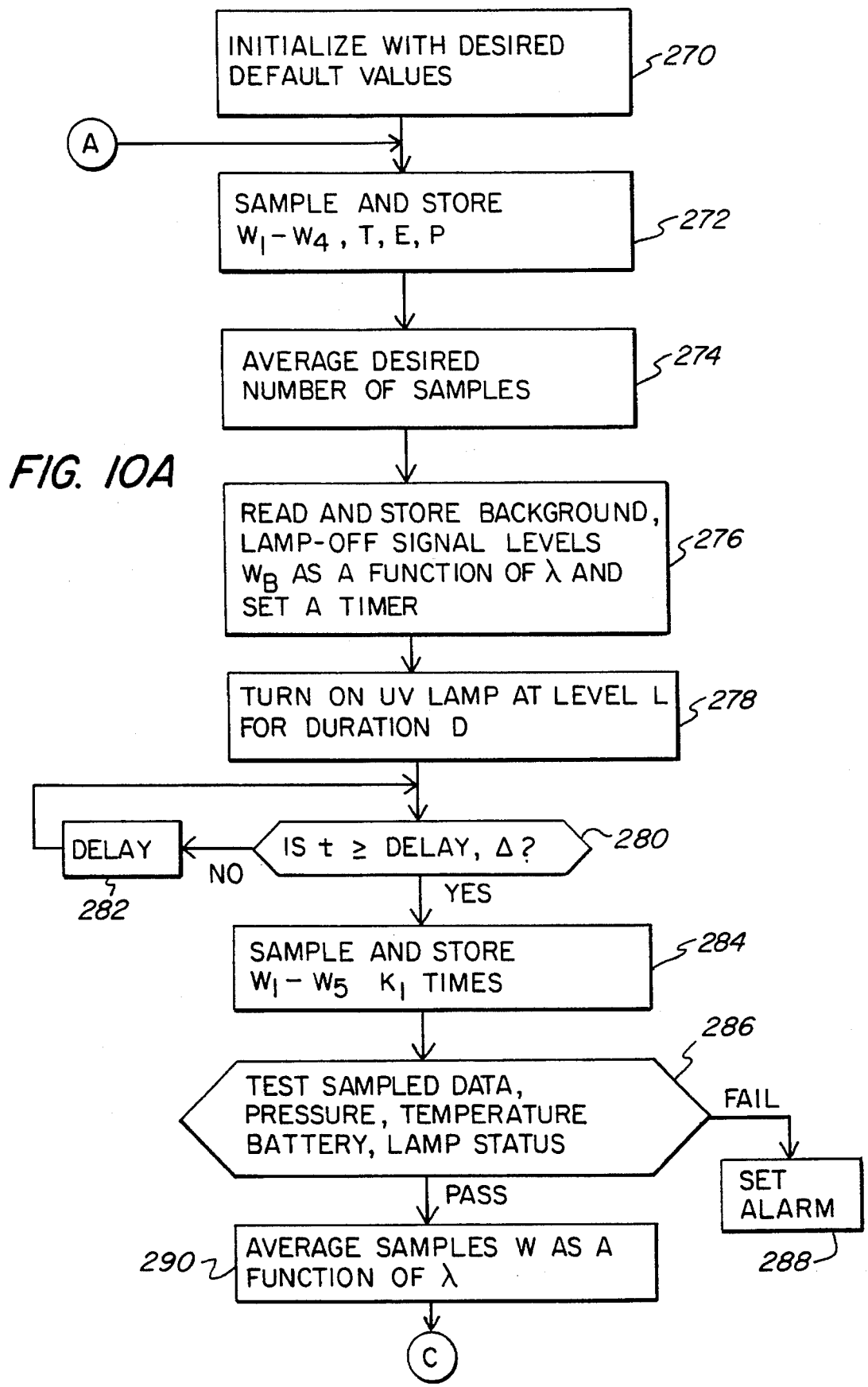
Figure 10B:
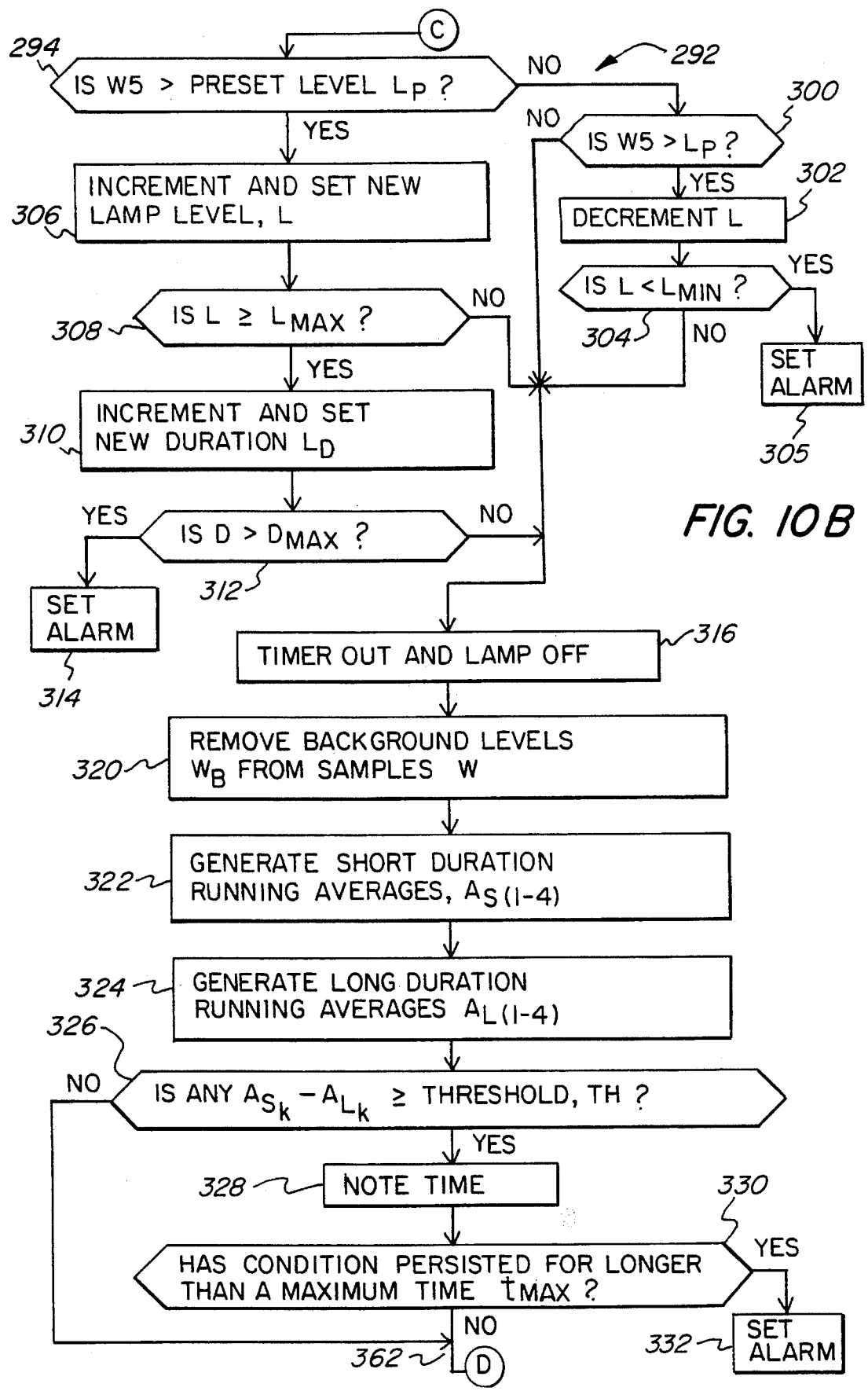
Figure 10C:
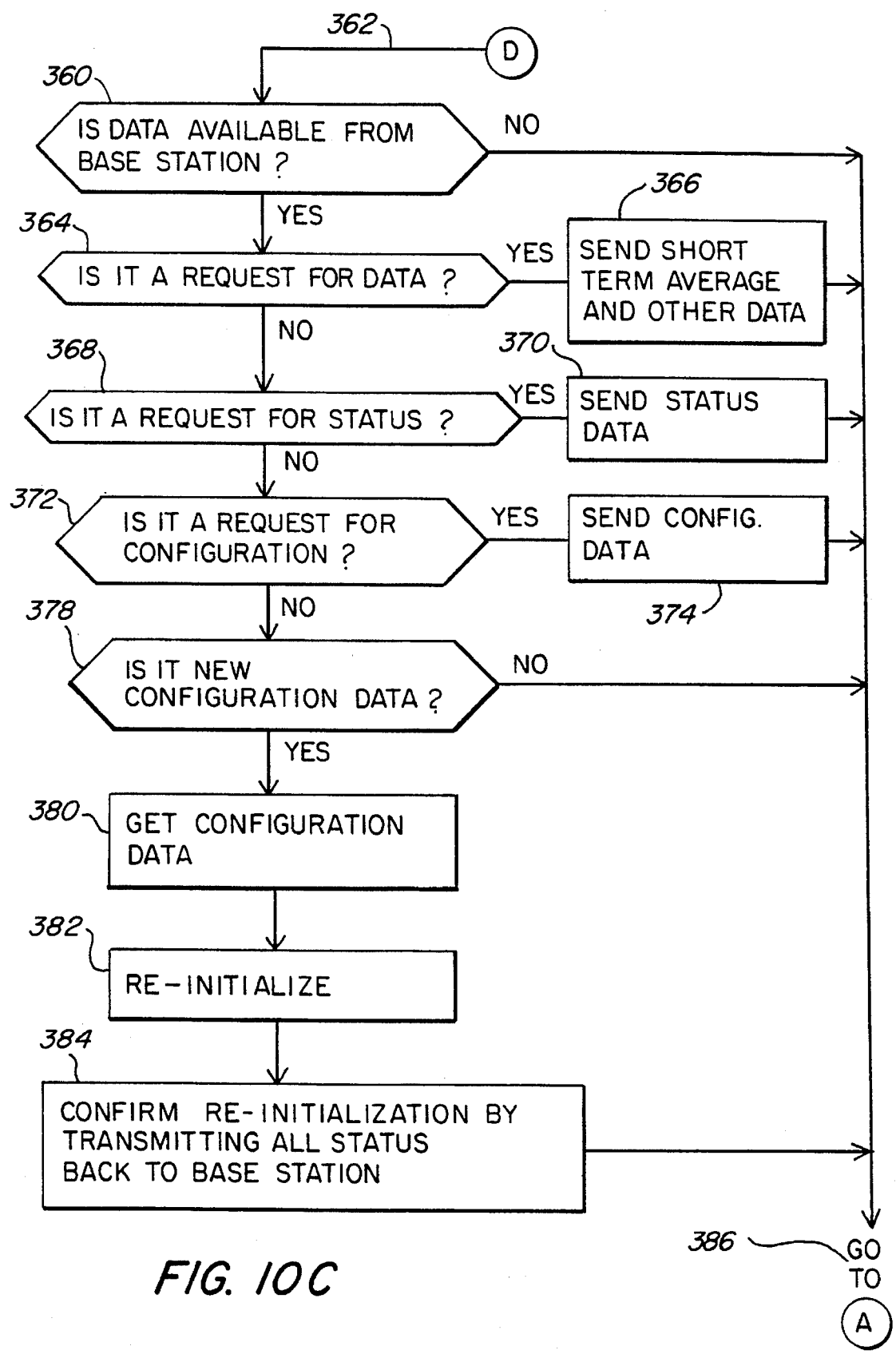
Figure 13:
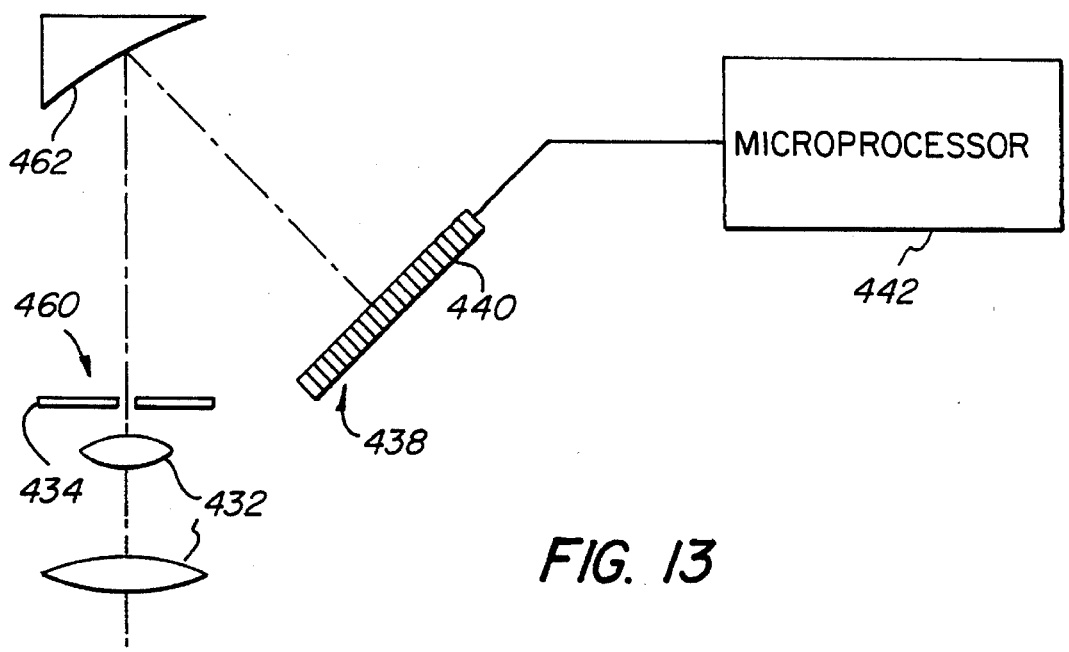
Figure 12:
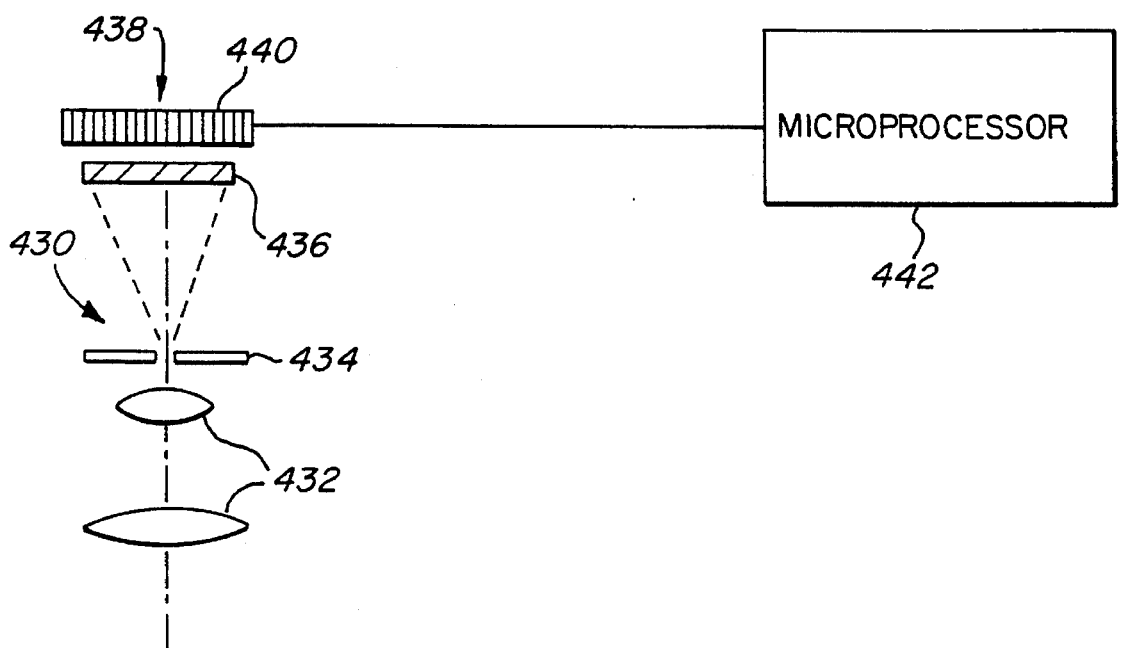
Figure 14:
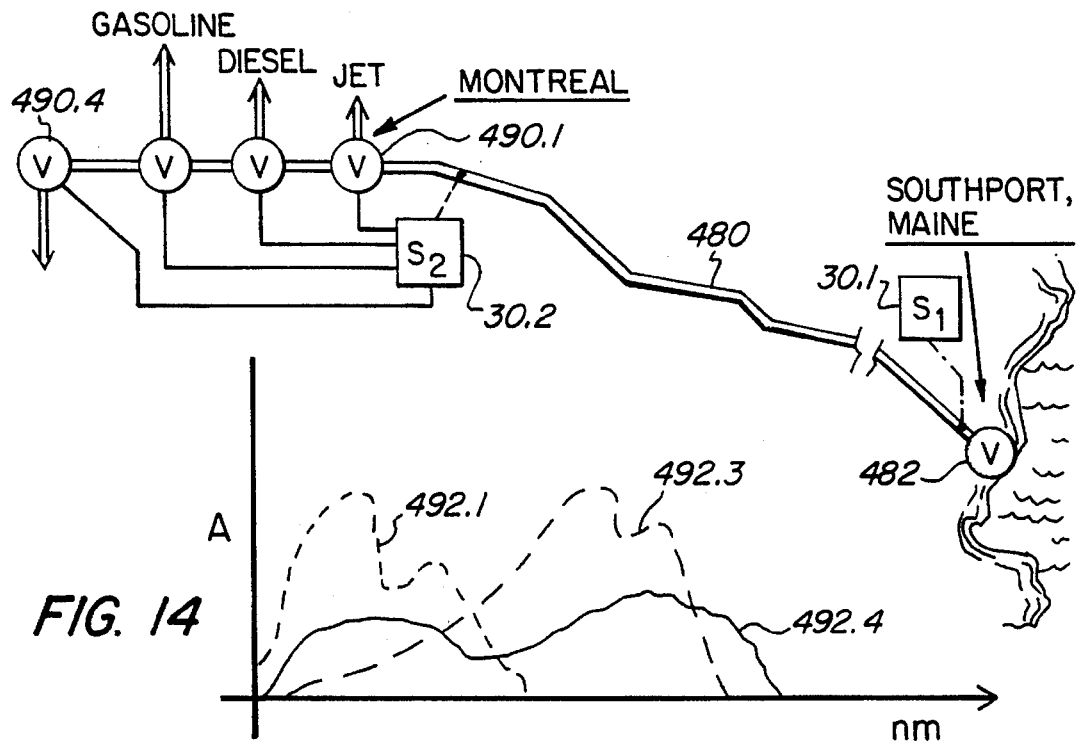
Figure 15:
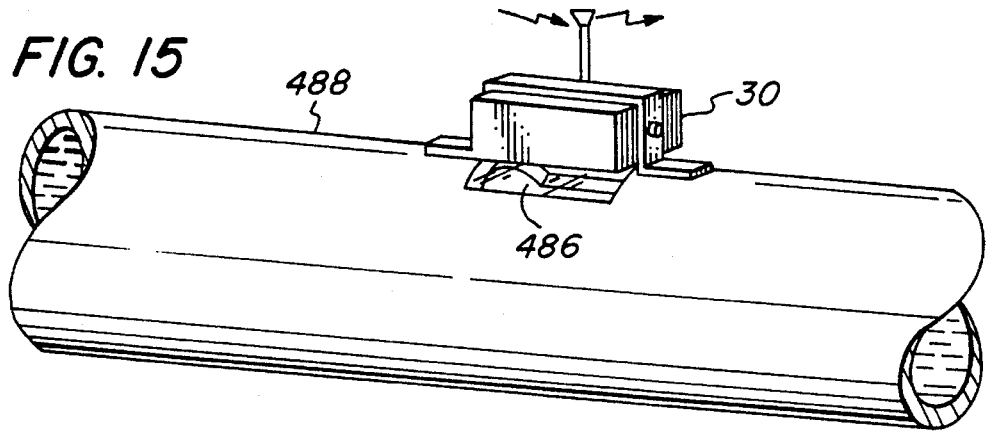
Figure 16:
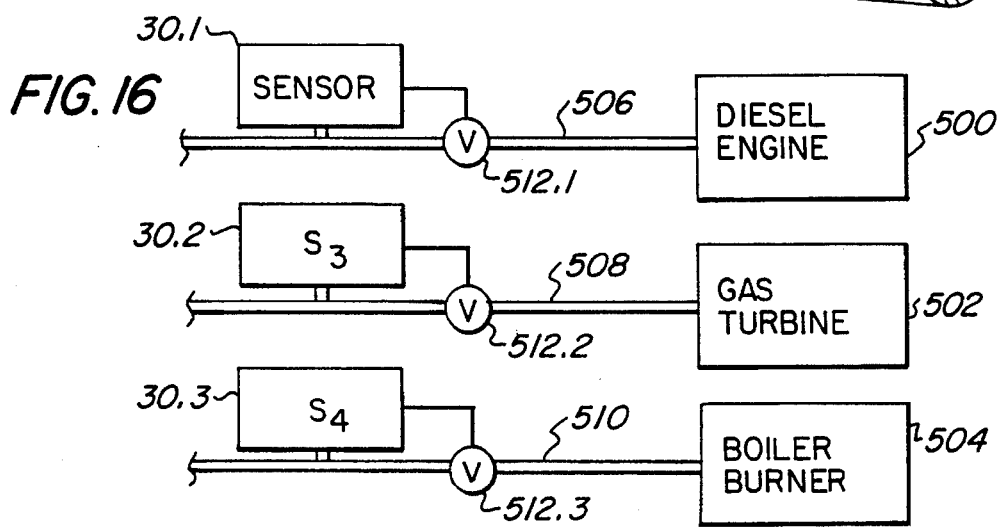
Figure 17:
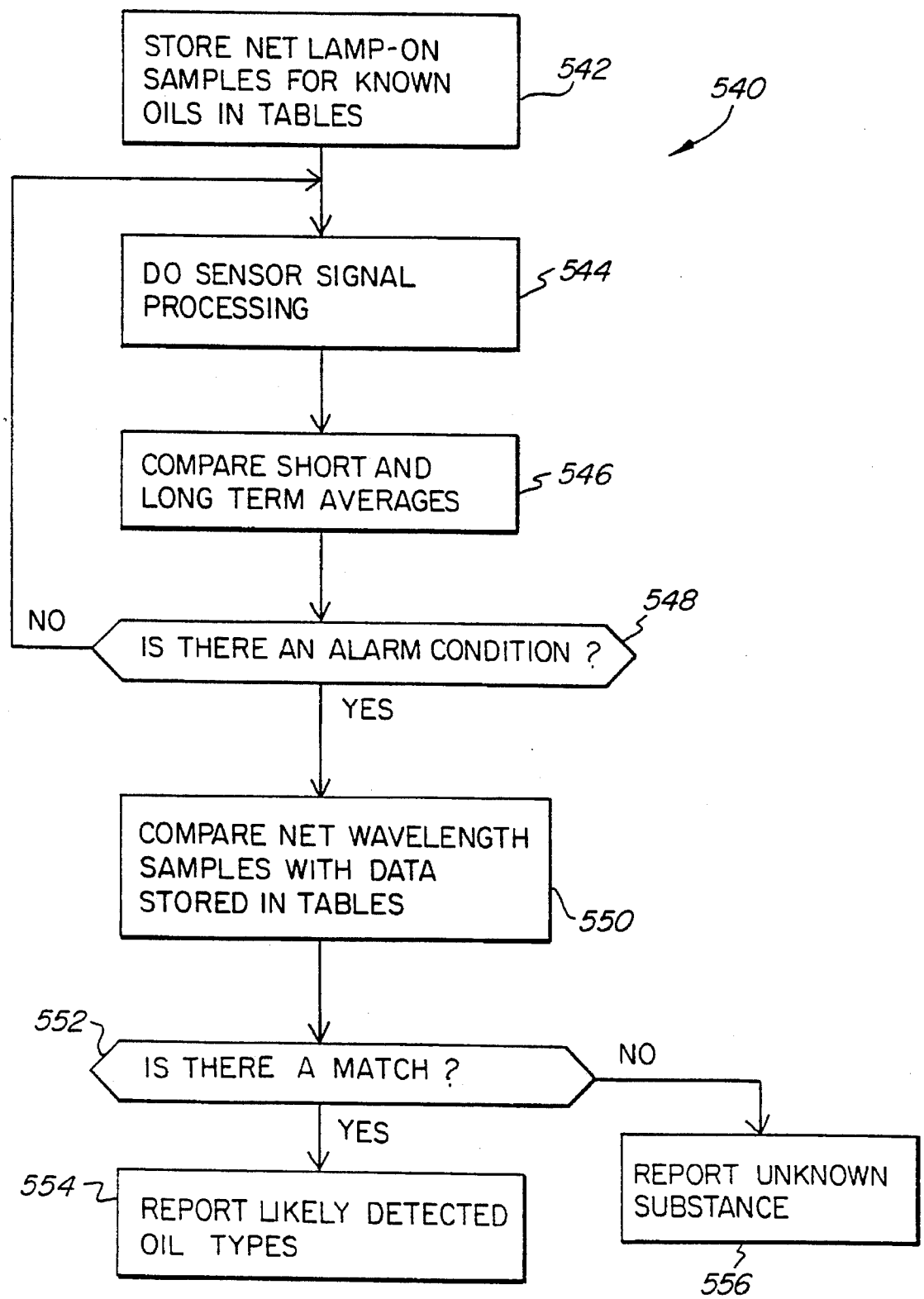

FIGS. 10A, 10B, and 10C are related flow charts for a microprocessor used in the sensor shown in FIG. 8;

FIG. 11 is a compilation obtained with a standard fluorimeter of fluorescence response curves for various oils as a function of detected amplitudes and for different optical wavelengths;

FIG. 12 is a schematic view of an alternate optical detector for use in the buoy system of FIG. 8;

FIG. 13 is a schematic representation of another optical detector for use in the buoy system of FIG. 8;

FIG. 14 is schematic representation of a control system using the fluorescence sensor of this invention in the management of the operation of a pipeline;

FIG. 15 is a perspective view of the mounting of a sensor of this invention on a pipe to detect chemicals such as oil passing therethrough;

FIG. 16 is a schematic representation of a sensor of this invention to detect and protect against the supply of a wrong fuel to an engine or burner; and FIG. 17 is a flow chart for the identification of different oils with a sensor of this invention.

DETAILED DESCRIPTION OF DRAWINGS

Figure 1A:
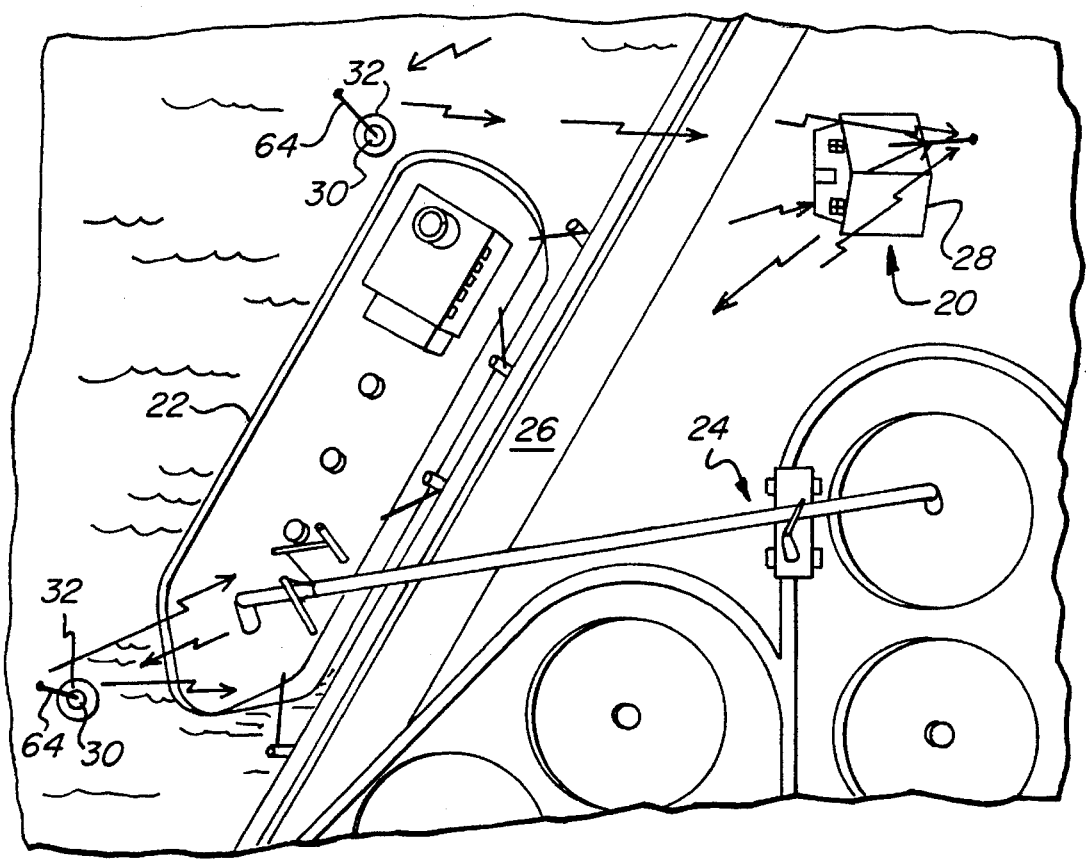
FIG. 1A is a plan view of a system in accordance with the invention for the detection of oil spills from a tanker at a dockside.
Figure 1B:
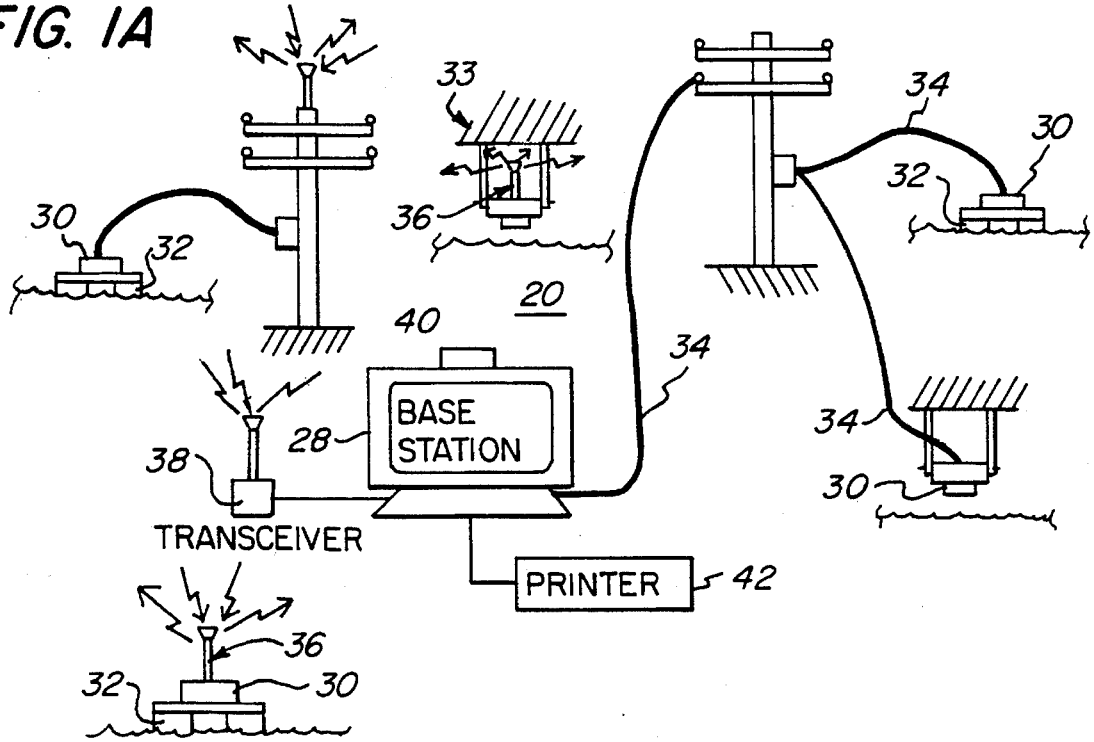
FIG. 1B is a schematic block diagram representation of a spill detection system in accordance with the invention.

With reference to FIGS. 1A and 1B, an oil spill detection system 20 is shown for use, for example, around an oil tanker 22 tied to a pumpout station 24 at a dockside 26. System 20 includes a base station 28 and one or more sensors 30 which may be either placed on buoys 32 or suspended at a fixed location such as at 33. The sensors 30 are self-contained portable devices in that they are battery operated and hermetically-sealed under pressure by an inert gas such as argon. Sensors 30 use an explosion proof housing and with the inert gas pressurization provide extra assurance for safe operation in a hazardous area.

System 20 employs a plurality of sensors 30 under the control by base station 28 which can communicate with the sensors 30 by way of direct cables 34 or via radio telemetry. The base station 28 serves as the primary operator system interface and maintains full bidirectional communication with each sensor to assure fail-safe operation. Hence, several sensors 30 have transceivers 36 capable of two-way communication with a compatible transceiver 38 at the base station 28. Particular techniques and protocols for requesting, transferring and handling of data between the base station 28 and sensors 30 are well known and are not further described herein.

Base station 28 includes a microprocessor-type computer with suitable programs for the management of the data from the various sensors 30 and the display of data from the sensors using an appropriate video terminal 40 and printer 42.

Figure 2:
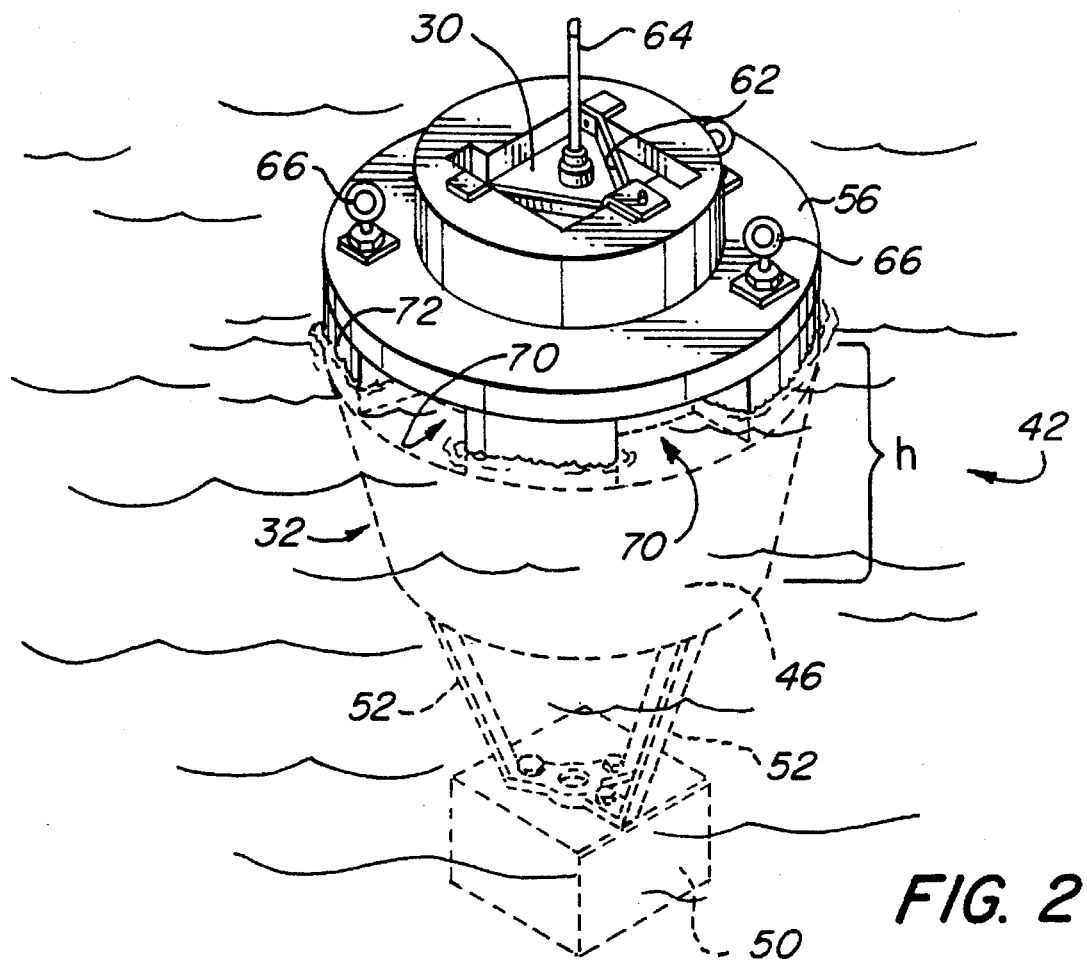
FIG. 2 is a perspective view of a buoy system in accordance with the invention.
Figure 3:
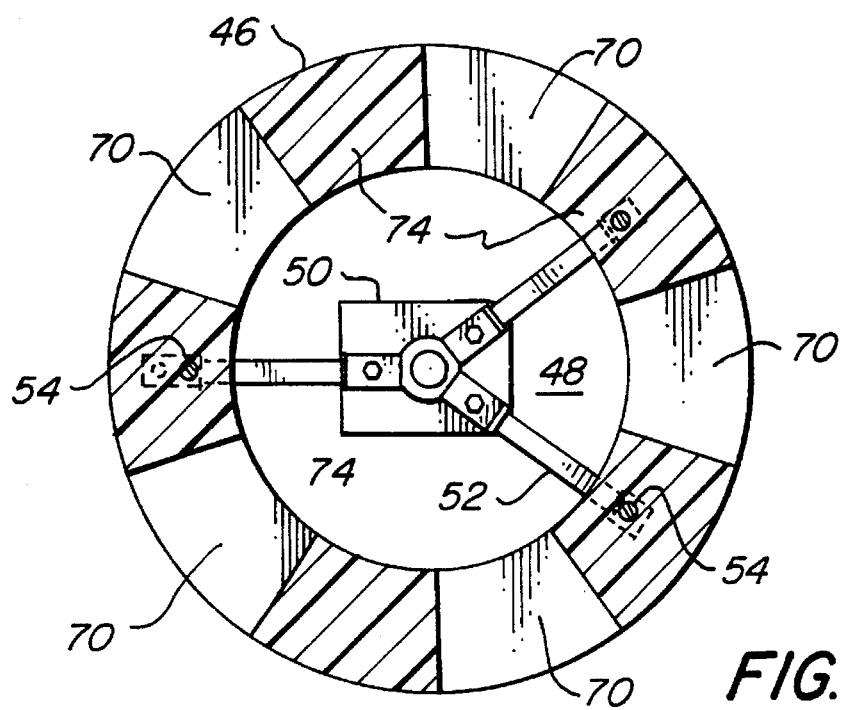
FIG. 3 is a horizontal section view of the buoy system of FIG. 2 taken above the water line but below the sensor and looking down.
Figure 4:
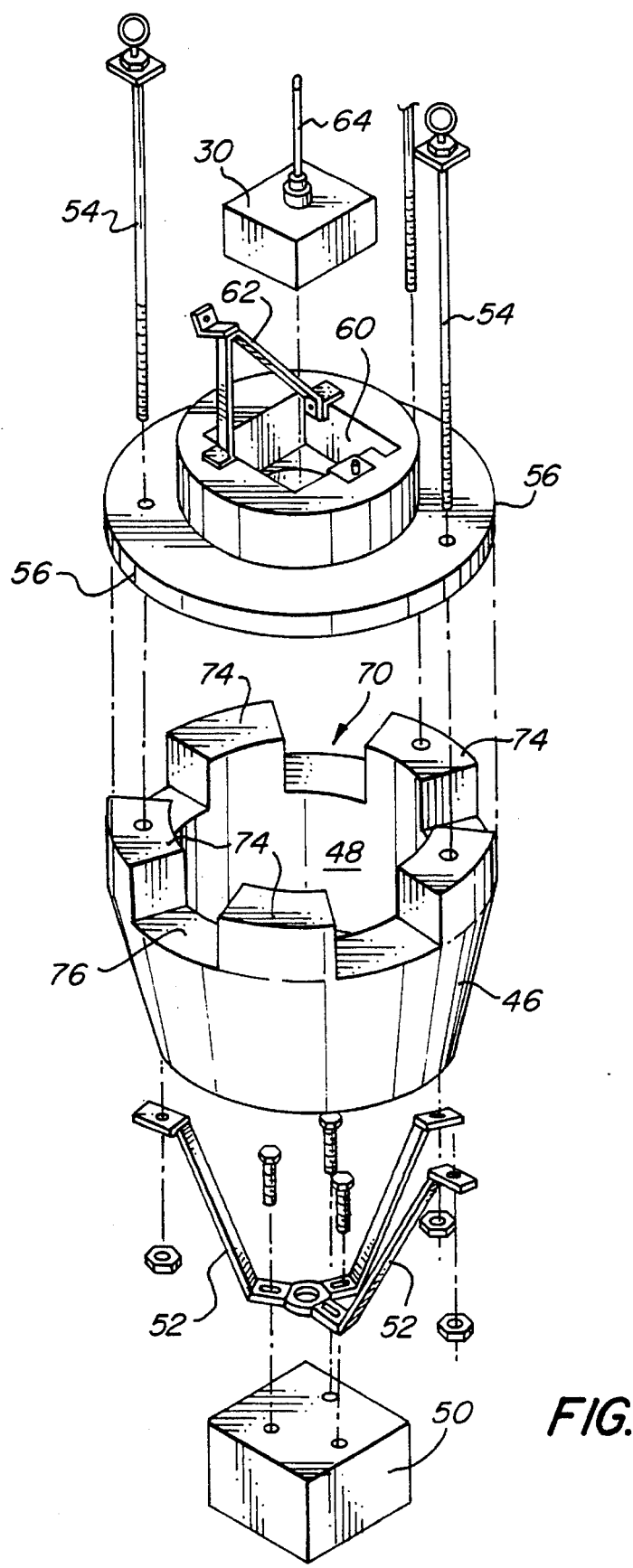
FIG. 4 is a perspective exploded view of the buoy system of FIG. 2.

With reference to FIGS. 2–5, a buoy system 42 is shown formed of the combination of a sensor 30 and a buoy 32. The buoy 32 is formed of a thick-skinned impact and abrasion-resistant foamed, closed cell, thermoplastic material. The buoy 32 has a conically-shaped wall 46 surrounding an inner cavity 48. The cavity is open on the bottom to deep water. Below the wall 46 is a deeply-suspended ballast 50 connected to the wall 46 with stainless steel struts 52. The number of struts 52 is limited to reduce their inducements of waves inside cavity 48 as a result of buoy motion. Stainless steel tie rods 54 extend through the wall 46 to connect to the struts 52 and clamp a cover 56 over the top of wall 46. Cover 56 has a mounting aperture 60 shaped to seat a sensor 30. A clamp 62, which is pivotally attached to cover 56, is used to fix sensor 30 firmly in place. In the view of FIGS. 2 and 4, an antenna 64 extends above sensor 30 though it should be understood that the sensor 30 can be connected to a cable instead. The rods 54 also have eye hooks 66 to provide hard points for the lifting and handling of the buoy system 42.

A particularly significant feature of buoy 32 is its windows 70 which extend below the water line 72 to allow flow of surface water beneath sensor 30. There are five windows 70 evenly spaced around a central axis and the sensor 30. Opposite each window 70 is a vertical wall segment 74 which tends to enhance the reflection of waves entering from an oppositely-located window 70 so that the reflected wave can pass back out through a window.

The buoy 32 has a very low center of gravity well below the center of buoyancy and has a substantial portion of wall 46 extending below water line 72. As a result, buoy 32 provides a stable platform in high water currents and with moderate harbor wave conditions. The buoy is intended to reflect the energy of deep water waves whose length are generally less than about twice the depth of floatation of the portion, h, of wall 46 below water line 72.

The windows 70 are selected in size so as to provide, while taking the ballast 50 and buoyancy of the system into consideration, as shown in FIG. 5, a shallow entry of depth $h_g$ for surface water. The bottoms 76 of windows 70 are thus preferably generally about an inch below water line 72. The inner surface 78 of wall 46 is intended to drop off sharply from window bottom 76, such as at a right angle.

With a buoy 32 of this invention, large waves tend to be reflected as suggested by arrows 80. Smaller waves, such as 82, capable of entering windows 70, as suggested by arrows 84, steepen in height above the shallow threshold bottom 76 but when they encounter the sharp drop off at wall 78 with much deeper water inside cavity 48, the wave 82 is much reduced in height.

As a result, the wave heights and water disturbances inside cavity 48 can be significantly limited, yet sufficient depth across the window bottom 76 permits a flow of surface water through the windows into the cavity and below sensor 30 to reveal the presence of an oil slick.

The horizontal dimensions of cavity 48 are selected sufficient to block wind effects on the water surface inside. Hence, the cavity 48 should not be so large as to enable a significant build up of waves due to wind. Yet, the cavity should not be so small that light entering windows 70 will significantly interfere with the operation of sensor 30. In one effective buoy in accordance with the invention, the wall 46 had an outer diameter at cavity 48 of about 32 inches and had a wall thickness of about six inches to form a cavity of about 20 inches in diameter. The windows lateral widths extended generally the same angular distance as the adjacent wall segments 74, or about 36 degrees. The vertical height of windows 70 preferably is made as low as practical to enhance shielding of sensor 30 from external ambient UV light such as may arise from sunlight or mercury gas type lighting as is commonly encountered at dock sides.

With reference to FIG. 7, a sensor 30 in accordance with the invention is shown with greater detail. The sensor 30 includes a hermetically-sealed housing 90, generally rectangular in shape both in the view in and out of the plane of the paper and has a bottom-located quartz window 92 in a bottom portion 94. The window 92 is capable of passing the optical wavelengths of interest. The bottom portion 94 of housing 90 is circular and is formed with screwed-on annular segments 96, 98, which enclose and also provide access to an optical assembly 100. Appropriate sealing techniques are used to render housing 90 explosion proof.

The optical assembly 100 is formed of an annular UV light lamp 102 which surrounds a central optical light collector and light detector assembly 104. The excitation UV lamp 102 preferably is a low pressure iodine doped mercury discharge lamp using a commercially available silica UV transmissive tube. The lamp 102 with its tubing are selected to maximize optical energy at a wavelength of about 254 nanometers (nm) while blocking the transmission of ozone-producing energy emitted at 195 nm wavelength.

Lamp 102 is mounted in a correspondingly-shaped aluminum housing 106 which aids in reflecting UV light towards underlying water in the buoy 32 or such other medium to be exposed to a fluorescence stimulating energy. Lamp 102 is operated in a pulsed mode, both to provide a UV peak power, save battery power, and enable a measurement of background noise to be subtracted from lamp-on detected signals.

An optical detector 108 is disposed over lamp 102 to provide an electrical signal W5 on a line 110 representative of the temperature of the gas inside lamp 102 and the energy emitted at 254 nm. A light-blocking iris 112 is interposed in front of the detector 108 which is also so selected as to be relatively insensitive to solar light. The electrical signal on line 110 is amplified and used to maintain the gas temperature inside lamp 102 at a substantially constant level. An appropriate automatic gain control loop, as will be further described, is used to regulate power supplied on lines 114 to lamp 102 to maintain the desired constant output level of energy at the 254 nm wavelength.

The optical detector assembly 104 includes a two element lens assembly formed of an aspheric positive lens light collector 120. This lens has an f number, or numeric aperture, of nearly 1.0 to enhance light collection while maintaining a minimum physical size. The second lens 122 is a negative lens of proper focal length to provide an exit beam 124 (see FIG. 8) of concentrated quasi-collimated light. The lens assembly, sometimes referred to as a Barlow lens system, is selected to provide an efficient collection of fluorescent energy emitted from the UV irradiated water surface. As shown in FIG. 8, the beam 124 is directed in a vertical path through an optical filtering column selected to extract specific predetermined wavelengths, w.

With further reference to FIGS. 7 and 8, at selected locations along the optical column are 45 degree oriented dichroic beam splitters 128.1–128.4 that reflect predetermined wavelength regions of the collected light in beam 124. The first beam splitter 128.1 reflects light in the range of 293 to 310 nm along an optical channel 130 which is at 90 degrees relative to beam 124. Splitter 128.1 passes substantially all of the wavelengths above this upper wavelength value.

A second beam splitter 128.2 reflects all wavelengths longer than 470 nm along an optical channel 132 parallel to channel 130 and passes all shorter wavelengths along the column.

A third beam splitter 128.3 reflects all wavelengths in the range from 380 to 429 nm along an optical channel 134 and passes the remaining energy to a splitter 128.4 which reflects optical wavelengths in the range from 320 to 360 nm along an optical channel 136.

Within the channels 130, 132, 134, 136, narrow band optical interference filters 140.1–140.4 are located to select specific wavelengths, respectively at 293, 492, 394, and 348 nm, which are then detected by blue enhanced silicon photodiodes 144.1–144.4. The diodes convert incident optical energy into electrical signals W1, W2, W3, W4, which correspond to the detected light at respectively successively longer wavelengths.

The wavelength signals W1–W5 are amplified and electronically filtered and adjusted to signal levels that are compatible with an analog-to-digital (A/D) converter within a microprocessor controller 150 mounted inside housing 90. A rechargeable battery 152, transceiver 154, and various electronic processing circuits as hereafter described are also inside housing 90. A temperature sensor 156 and pressure sensor 158 are located inside housing 90 to enable monitoring of these housing parameters by a base station 28. Battery voltage level is monitored by a detector 160 which produces a signal representative of available battery power on a line 162.

The optical assembly 104 is enclosed in a shield 163 see FIG. 7 and is mounted on a plate 164 which is in turn mounted with compressible supports 166 to a plate 168 attached to housing 90. The transceiver 154 is connected to antenna 64 through a connector 170 which also serves as a valve through which the air within housing 90 can be purged and replaced by an inert pressurized gas, such as argon.

With further particular reference to FIGS. 8, 9, and 10A–10C, the outputs from photodiodes 144 are amplified with AC amplifiers 180.1–180.5 to reduce the effects of both continuous (stead state) and certain varying light signals. The preamplifiers 180 are AC coupled and tuned to provide maximum gain at a lamp excitation frequency that is referenced with respect to a dark or background level sampling. This feature provides a very effective filtering out of undesired electro-optical noise signals prior to conversion to digital format.

The analog signals produced by optical detectors 108 and 144, the parameter signals P, T, and E are multiplexed onto a single line 182 by a sample and hold multiplexer and A/D converter 184 that are part of the microcontroller 150. For each cycle that lamp 102 is ON and OFF, the microcontroller 150 is programmed to average a number of A/D conversions associated with each optical channel 130, 132, 134, and 136. The number of samples for each channel can vary; however, four samples have been found sufficient to yield a value for an optical channel.

The microcontroller then turns the excitation lamp 102 off. After a delay another series of conversions on the detectors 108, and 144 signals are made to form background level signals. The digitized values of the background level signals are then subtracted from the digitized lamp ON signals to in effect eliminate noise signals present at the outputs of the optical detectors.

Since optical noise from man-made UV sources, such as 50 or 60 cycle mercury arc lamps introduce cyclical noise, this can be effectively filtered out. This is done by selecting the delay commensurate with the cycle time associated with the mercury arc lamps. At 50 Hz this cycle time is 20 ms and at 60 Hz, 16.67 ms. By selecting the delay at some whole multiple of the cycle time, the same noise level from such extraneous UV sources can be effectively eliminated.

In an alternate operation as described with reference to FIGS. 10B and 10C, the background levels are sampled first and then after a simila fixed time delay the lamp ON levels are sampled. selecting the delay at some whole multiple of the cycle time, the same noise level from such extraneous UV sources can be effectively eliminated.

In an alternate operation as described with reference to FIGS. 10B and 10C, the background levels are sampled first and then after a similar fixed time delay the lamp ON levels are sampled.

In the buoy system embodiment described herein, a microcontroller 150 having a programmable microprocessor is employed. It should be understood, however, that hardware can be used to implement the functions of the microprocessor.

Hence, the digitized samples from the multiplexer 184 are respectively accumulated in storage registers or memory locations associated with respective optical channels and whether the samples were made during a lamp OFF condition, or a lamp ON state. Lamp OFF samples are stored at 190 and lamp ON samples are stored at 192. The lamp OFF sample values are then subtracted at 194 from respective lamp ON samples and the differences accumulated at respective short and long term registers at 196 and 198 for the respective optical channels 130–136 and then averaged.

The term averaging here contemplates in a first instance the simple arithmetic accumulation of a predetermined number of samples and dividing the sum by this number. Other techniques, however, can be used to determine sample values which are representative of the trends of the fluorescence activities in the respective samples. Such other techniques are intended to be included in the term "average" as this is used herein.

The accumulation of the optical channel samples at 196 is intended to produce a running average, $A_s$, over a relatively short time interval and thus may involve relatively few sampling cycles, say from 8 to 16, as may be selected at 200, either as a preset or from a remote base station. In practice, generation of a running average would involve, for example, storing in fixed locations the last eight samples and then adding them together and dividing the total by the number of samples. After each running average determination, the samples are shifted in location and the last sample stored in a vacated location. In this manner, a signal truly representative of short term trends in the fluorescence behavior in the respective optical channels is obtained.

In a similar manner, a long term running average, $A_L$, is derived at 198 using a much greater number of samples as determined at 202 either by way of a preset or from the base station. The number of samples is of the order of 256 or 512 samples. The long term running average is thus representative of a long term trend.

The short term running average values $A_S$ are transmitted at 204 to the base station 28. Such transmission can occur also upon transmitted request at 206 from the base station. Data is transmitted back to the base station in short signal bursts. The base station may then use this information to produce its own long term running average $A_L$ and conduct a data analysis as will be further described.

At 210 the long term running averages $A_L$ are subtracted from short term averages $A_S$ for respectively like optical channels. When the differences exceed a threshold level, as is preset at 212 for each of the optical channels, a primary condition for an alarm has been detected at 214, and a signal indicative thereof is produced, and the time of its occurrence is stored.

A second condition for the detection of an alarm is that the alarm condition detected at 214 persists in excess of a predetermined time as preset at 216. The time interval during which the condition detected at 214 persists is then measured at 218, and if it exceeds the preset value, an alarm is set off at 220 and transmitted at 222 to the base station.

FIG. 9 graphically illustrates how an alarm condition is detected. Curve 224 represents the magnitude of short term running average values for one optical channel. Curve 226 represents the magnitude for long term running average values for the same optical channel. If an oil slick were to pass below the sensor 30, then the initial response is observed with the short term curve 224, since the values for the long term curve 226 do not respond as quickly. When at time $t_1$, the difference between curves 224 and 226 exceeds the threshold value, $T_h$, as set at 212, a preliminary alarm condition occurs. If after a time interval, as set at 216, at time $t_2$, the short term curve still exceeds the threshold, an alarm is set.

If the substance below the sensor 30 disappears before the passage of the time interval $t_2-t_1$, or if an ambient brief transient UV interference signal caused the initial alarm condition, then the short term average drops and follows the curve 230. Since the alarm condition no longer exists, appropriate flags are reset.

Since the momentary alarm condition did increase the short term average value, the long term average continues to increase, even though the condition that caused its increase no longer qualifies as an alarm. In such case, the long term curve 226 can be brought back to the steady state level 232 by temporarily, as long as no new alarm condition arises reducing the number of samples needed to produce a long term running average. This would enable the sensor to more quickly recover from momentary preliminary alarm conditions.

The effectiveness of sensor 30 is significantly enhanced by use of an automatic control loop 240 for maintaining the main excitation wavelength, 254, nm, at a constant level. This, as previously mentioned, involves the use of detector 108 whose output signal W5 has an amplitude level representative of the excitation level, the internal gas temperature, of lamp 102 at 254 nm.

After sampling and conversion to a digital format, a number of the samples, such as four, during each lamp ON state, are averaged at 242 and the average compared at 244 with a predetermined desired level, $L_p$, that is preset at 246. Any error $\epsilon$ is then used by a lamp control signal generator 248 to adjust the lamp gas temperature. Two control signals are produced to set the lamp gas temperature, a voltage level, L, which is set on line 248, and a lamp duration signal, D, set on line 250. Both control signals are applied to a lamp driver 252 after the lamp voltage level control signal is first converted to analog form with a D/A converter (not shown). Battery or power supply power is also applied on line 254 to the lamp driver 252. The output from lamp driver 252 on line 114 has an amplitude and pulse duration commensurate with what is necessary to drive the error signal $\epsilon$ to a minimum level.

In this manner, by selecting a consistent measuring detector 108 and a common preset level at 246, different sensors 30, as for example employed in the manner of FIGS. 1A and 1B, will respond in a consistent and repetitive manner to the detection of fluorescing substances. The sensor 30 may then also be reliably employed to characterize or identify somewhat similar but fluorescingly distinctive oil products.

FIGS. 10A, B, and C illustrate with greater detail a flow chart for operation of a microprocessor in the controller 150. At 270, initialization steps are carried out such as for the lamp power signal and for certain default values for parameters necessary to automatically detect the occurrence of an oil spill. In addition, the UV lamp 102 is initially set to OFF.

At 272, digital samples of all optical channels W1–W5 and parameters such as the battery voltage E, temperature T, and internal gas pressure P are taken. In the case of the optical channels, the samples represent dark noise or background noise levels, $W_B$. Preferably, a number of samples are taken at this time and averaged at 274.

At 276, the background noise signals $W_B$ are sampled at a particular time as a function of the wavelengths associated with the optical channels 230–236 and a timer is set a essentially the same time. Typically, four samples are taken in a very short time measured in microseconds and then averaged.

At 278, the UV lamp is turned on at a power level L and for a duration D.

At 280, a step is taken to determine when a delay, delta, has occurred after the time the $W_B$ signals were sampled at step 276. The delay is a whole multiple of the natural AC cycle time of ambient lighting as may be used. For a 50 Hz frequency, a 50 milliseconds delay (for five cycles) and for 60 Hz AC a similar delay for six cycles would work. The delay max involves a waiting step such as at 282. The delay also should be sufficiently long so that transient will have decayed.

The effect of delaying the sample at 284 of the lamp ON optical channels until just after the expiration of the delay of step 280 is that the background and lamp ON sampling occurs essentially at the same intensity levels of any extraneous AC drive UV light sources. Hence, subsequent removal of the background levels $W_B$ from the lamp ON signals W tends to also remove that type of source of noise. The number of lamp ON samples taken can be varied, however, four during any one measurement was found to be sufficient.

At 286, the various other parameters such as pressure, temperature, battery power and lamp status are examined against respective preset levels. If any one of the sampled parameters exceed the preset levels, an alarm condition is set at 288.

At 290, the lamp ON signals W are averaged and a short routine 292 is entered to regulate the lamp gas temperature. Thus, at 294 the lamp monitoring signal W5 is tested for whether it exceeds the preset level $L_p$ set at 246 in FIG. 8. If not, a test is made at 300 whether the signal W5 is less than the preset and if so, the lamp power level L is decremented at 302 as long as it is not less than a minimum acceptable level as determined at 304.

If the lamp level signal W5 does not exceed the preset level $L_p$, the power level L is incremented at 306 provided the new higher value does not exceed some maximum level $L_{MAX}$ as determined at 308. If this maximum level is exceeded, then at 310 the duration D for the lamp ON power pulse is incremented provided this does not exceed a maximum as determined at 312. If the maximum is exceeded, this means that the lamp cannot deliver the required energy level at the main excitation wavelength of 254 mm and an alarm is set at 314.

As indicated in the flow chart of FIG. 10, the results of the other tests in routine 292 lead to step 316 where the lamp 102 is turned OFF after the duration D as determined during a previous pass through routine 292 and the timer is reset.

Signal processing is then performed beginning at 320 where the background level signals are subtracted from the lamp On signals for the respective optical wavelengths. Short $A_{s(1-4)}$ and long $A_{L(1-4)}$ duration running averages are produced respectively at steps 322, 324.

At 326 tests are made whether the difference between any short term and long term signal for any one optical channel exceeds a threshold level associated with that channel. If so, the time is noted at 328, and at 330 a test is made whether this preliminary alarm condition for that optical channel has persisted for longer than a time $t_{MAX}$. If so, an alarm is set at 332.

With a sensor 30 in accordance with the invention, dependable signatures of various fluorescing chemicals such as different types of oil can be obtained. The signals can be detected during very different ambient conditions. Very thin patches of oil can be detected and distinguished from background fluorescing levels.

Identification and use of the data generated by a sensor 30 can be done inside it, but preferably is communicated to a base station such as shown at 28 in FIG. 1. At a base station, the various sensors 30 can be initialized with parameter values and presets appropriate for the condition associated for each sensor and for different ambient conditions. For example, a sensor at one location may be mounted in a buoy 32 and subjected to severe weather conditions that require different preset values from a sensor 30 located near a storage tank in a stable environment.

Hence, a feature of the invention is that sensor 30 can communicate with the base station and both receive new initialization data or send its own test results or other responses. FIG. 10C illustrates one flow chart for a sensor 30 microprocessor to enable it to respond to communications with a base station 28 as part of the regular program cycle. Thus, commencing with step 360 following line 362 in FIG. 10B, a test is made whether a communication was received from the base station.

If so, then at 364 a test is made whether it is a request for data, and if so, data is sent at 366. Otherwise, at 368 a test is made whether the request is for status, and if so, status data is sent at 370. The request can be for the configuration data of the sensor parameters, initial values and various constants as determined at 372.

In such case, this type information is sent to the base station at 374. Data received from the base station can be new configuration data as determined at 378. If so, the sensor gets and applies new configuration data at step 380 and re-initializes the sensor microprocessor at 382. A confirmation of the reinitialization is then made at 384 by sending a status back to the base station. All steps eventually lead to a return to the top of the program as set forth at step 386.

With a sensor in accordance with the invention, a broad variety of different hydrocarbon fuels can be not only detected but identified and distinguished from each other. FIG. 11 illustrates fluorescent characteristics at the wavelengths of the optical channels for different fuels, such as a solid bunker-type fuel 400 used by one power company, a jet fuel 402, a diesel fuel 404, a number 4 type of fuel 406, a number 6 fuel 408, a crude oil 410, and plain water 412. The numerical values below the curves were obtained with a different instrument than sensor 30 and used to select the particular wavelengths for the optical channels. The curves of FIG. 11 indicate that with a sensor 30, individual fuels can be identified. This would be particularly so when the illumination level by the UV lamp 102 can be held to a constant level and background noise can be consistently removed from the samples. The identification may thus not only be made by reliance of ratios of sample values associated with different channels but also with the use of absolute of sample values. The identification may be a best approximation. However, in the case of an alarm, even a best approximation can be a guide as to from where a particular spill arose.

A more precise identification of substances can be derived by sensing the fluorescence at high number of different wavelengths. FIG. 12 illustrates one optical column 430 for producing such higher resolution sensor. The column 430 includes appropriate field optical elements 432, an entrance-apertured mask 434 and a gradient optical interference filter 436. The latter's output is detected by an array 438 of photo diodes 440, each being located to detect a different wavelength. The outputs from the photo diodes 440 are fed to a microprocessor 442.

FIG. 13 illustrates a different arrangement 460 using an off-axis parabolic holographic grating 462 whose output is incident on an array 438 of photo diodes 440.

With a sensor 30 in accordance with the invention various commercial applications become possible. As shown in FIG. 14, a long oil pipe line 480 now connects an oil tanker terminal 482 in Southport, Maine, with Montreal, Canada. Various types of oil are transmitted successively through the pipe line. Currently, one type of oil is distinguished from another by the appearance of variously colored balls pushed by the oil being pumped through. Instead of assigning an individual to continuously watch a window for the arrival of the balls at Montreal, sensors such as 30 could be used. One could be mounted as illustrated in FIG. 15 to detect the fluorescence of oil passing beneath a transparent window 486 in the pipe 488. Sensor 30 would detect changes in the fluorescence characteristics of an oil and generate an alarm or set one of a series of values 490.1–490.4 to cause the different fuel to be fed into the proper storage tank (not shown).

Two sensors 30.1 and 30.2 could be used, one at the entry point in Southport and another as shown in Montreal. The fluorescence characteristics of the oil sensed at Southport could be transmitted to the Montreal site to alert the sensor 30.2 or the base station there to look for a matching pattern associated with the material being sent through. The sensor 30 could also be used to identify the particular pattern, 492.1–492.3 of the oils in the pipeline 480 and needed to be directed to a particular storage tank until the new oil arrived.

Sensors such as 30 can also be used to protect equipment. For example, as shown in FIG. 16, sensors 30.1–30.3 are located to sense the types of fuel being fed to various different engines used at a power plant, such as a diesel 500, a gas turbine 502, and a boiler burner 504. Sensors 30.1–30.3 could be used to monitor fuel being delivered through respective pipe lines 506, 508, and 510. If the wrong fuel is fed through, sensors 30 would detect that before harm is caused and either send an alarm or cause the shut-off of a valve 512 in the pipe line.

FIG. 17 illustrates a flow chart 540 for identifying a particular oil when a sensor 30 detects the presence of an oil spill. At step 542 values of signals from optical channels 230–236 are determined for a large number of oils. Preferably, the net values are those detected by photodiodes 144.1–144.4 of FIG. 8 less background noise levels. This results in a compilation of values for different wavelengths and different oils as for example illustrated below the curves in FIG. 11. These values are stored during step 542 in a base station memory as a function of wavelengths and types of oil.

At steps 544, 546, and 548, sensor 30 is operated and its signals are processed as described with reference to FIGS. 8–10. If an alarm condition is detected at step 548, the net optical signals wavelengths values, W1–W4, such as the short term running average values that caused the alarm condition are compared at 550 with the values stored at 542.

The comparing step can involve comparing of ratios and absolute values so as to obtain the best possible matches. The criteria for a match can be set as appears appropriately necessary to distinguish different oils.

If a match is found at 552, a display of the likely oil that was found is made at 554. If no match is found, the substance which triggered the alarm is reported as unknown at 556.

The sensor of this invention can be used in a broad variety of applications. For example, if one desired to determine the migration direction and speed of waste water in soil, one could dope the liquid water with fluorescein, a material which fluoresces, at a bright green wavelength 542 nm, and deploy a plurality of sensors at different locations. The sensors would be in effect "tuned" to detect and identify this substance. Similar approaches can be used within a plant to track various products or byproducts. Both fluorescing and phosphorescing substances can be detected and the term fluorescence as used herein is intended to encompass both.

Having thus described the invention in connection with various embodiments, its advantages can be appreciated. Variations of the various embodiments can be implemented by one skilled in the art without departing from the scope of the invention as set forth by the following claims.

What is claimed is:

1. A fluorescence sensor for the detection of natural or doped fluorescing substances such as oil or other chemicals comprising:

source means for periodically illuminating a zone with light which includes an emission at a desired wavelength selected to stimulate fluorescence from the substance;

means for maintaining the level of the emission of the desired wavelength at a substantially constant level;

means for detecting predetermined wavelengths of light in said zone and producing first and alternate signals indicative thereof; said first signals being representative of the amplitude level of fluorescence from a substance in the zone when said source means is on and said alternate signals being representative of background optical noise in said zone when said source means is off;

means responsive to said alternate signals for producing background signals representative of said background optical noise at respective predetermined wavelengths;

means for applying said background signals to respective first signals for the removal of portions attributable to said background optical noise and produce net first signals indicative thereof; and means responsive to said net first signals for generating an alarm when a said net signal associated with a predetermined wavelength exceeds a threshold level for a predetermined interval;

said alarm generating means including means responsive to the net first signals for producing short and long term running averages thereof;

means for determining the difference between short and long term running averages associated with respective common wavelengths; and means for generating a said alarm when a said difference exceeds a predetermined threshold level.

2. The sensor as claimed in claim 1 wherein said means for maintaining said emission level of the desired wavelength at a substantially constant level includes:

light detector means located to sense said source of light at said desired wavelength and producing a second signal indicative of the intensity thereof;

means responsive to said second signal for producing an error signal representative of the difference between said second signal and a desired intensity level of said source of light at said desired wavelength; and means responsive to said error signal for regulating the power to said source of light so as to reduce the error signal.

3. A fluorescence sensor for the detection of natural or doped fluorescing substances, such as oil or other chemicals comprising:

light source means for periodically generating a beam of light which includes an emission at a desired wavelength selected to stimulate fluorescence from the substance and directing said beam of light to illuminate a zone;

means for detecting predetermined wavelengths of light in said zone and producing first and alternate signals indicative thereof; said first signals being representative of the amplitude level of fluorescence from a substance in the zone when said beam of light is on and said alternate .signals being representative of background optical noise in said zone when said beam of light is off;

means responsive to said alternate signals for producing background signals representative of said background optical noise at respective predetermined wavelengths;

means for applying said background signals to respective first signals for the removal of portions attributable to said background optical noise and produce net first signals indicative thereof; and means responsive to the net first signals for producing short-term running averages and long-term running averages thereof;

means for comparing said short- and long-term running averages to produce a comparison signal; and means for generating an alarm signal when said comparison signal exceeds a predetermined threshold value.

4. The fluorescence sensor as claimed in claim 3 and further including:

means for generative said alarm signal when said comparison signal exceeds said predetermined threshold value for a preselected duration.

5. The fluorescence sensor as claimed in claim 4 and further including:

means for resetting the long-term running average to a preset level when the comparison signal fails to exceed the threshold value for said preselected duration.

6. The fluorescence sensor as claimed in claim 3 and further including:

means for maintaining the level of the emission of the desired wavelength from the light source means at a substantially constant level.

7. The fluorescence sensor as claimed in claim 6 wherein said means for maintaining the emission level from the light source means substantially constant includes:

light detector means located to sense said beam of light at said desired wavelength and producing a second signal indicative of the intensity thereof;

means responsive to said second signal for producing an error signal representative of the difference between said second signal and a desired intensity level of said beam of light at said desired wavelength; and means responsive to said error signal for generating a pulse signal that is applied to said light source means and whose amplitude level is selected so as to reduce the error signal and maintain the emission level of the light source means substantially constant.

8. The fluorescence sensor as claimed in claim 3 and further including remote receiving means; and transmitter means for sending to a said remote receiving means a signal representative of said alarm.

9. A fluorescence sensor for the detection of natural or doped fluorescing substances, such as oil or other chemicals flowing through a conduit, comprising:

means for generating a beam of light which includes an emission at a desired wavelength selected to stimulate fluorescence from the substance and directing said beam of light to illuminate a zone in the conduit through which the substance flows;

means for detecting a predetermined wavelength of light stimulated by said beam of light and producing a first signal indicative thereof;

means responsive to said first signal for determining whether said substance flowing through the conduit is of a predetermined type or is of another type and producing a second signal indicative thereof; and means responsive to said second signal for sending an alarm signal when said second signal represents a substance different from said predetermined.

10. The fluorescence sensor as claimed in claim 9 and further including:

valve means interposed in said conduit to direct the flow of said substance in accordance with said alarm signal.

11. The fluorescence sensor as claimed in claim 9 wherein said first signal producing means includes means for detecting predetermined wavelengths of fluorescent light stimulated by said beam from the zone in the conduit and producing a plurality of first signals respectively indicative of the predetermined wavelengths;

means responsive to the first signals to determine the presence of a preselected substance flowing through the conduit and producing an identifying signal indicative of the presence said substance.

12. The fluorescence sensor as claimed in claim 9 and further including:

means responsive to said second signal for controlling the flow of said substance through the conduit.

* * * * *